(12) United States Patent
Hwa

(10) Patent No.: US 7,223,423 B2
(45) Date of Patent: May 29, 2007

(54) SKIN TREATMENT COMPOSITION

(76) Inventor: Julie Y. Hwa, P.O. Box 5345, Hagatna, GU (US) 96932

( * ) Notice: Subject to any disclaimer, the term of this patent is extended or adjusted under 35 U.S.C. 154(b) by 0 days.

(21) Appl. No.: 11/034,995

(22) Filed: Jan. 12, 2005

(65) Prior Publication Data

US 2005/0152867 A1   Jul. 14, 2005

Related U.S. Application Data

(60) Provisional application No. 60/536,070, filed on Jan. 12, 2004.

(51) Int. Cl.
*A61K 36/00* (2006.01)
(52) U.S. Cl. ..................................... 424/725
(58) Field of Classification Search ............... 424/725
See application file for complete search history.

(56) References Cited

U.S. PATENT DOCUMENTS

2004/0126342 A1*  7/2004  Dicianna .................... 424/59

FOREIGN PATENT DOCUMENTS

| CN | 1372910 | * | 10/2002 |
| JP | 405331034 | * | 12/1993 |
| JP | 2001122731 | * | 5/2001 |
| JP | 2001226219 | * | 8/2001 |
| JP | 2003342122 | * | 12/2003 |

OTHER PUBLICATIONS

Internet website "Cook Islands Biodiversity"- 'Pachira aquatica' (2 pages total).*
Information regarding Eagle wood (Chenxiang) [online] [retrieved on Jan. 12, 2005] Retrieved from the Internet : <URL: http://www.herbalshop.com/tcm/ChineseHerb_E119.html.

* cited by examiner

*Primary Examiner*—Christopher Tate
*Assistant Examiner*—S. B. McCormick-Ewoldt
(74) *Attorney, Agent, or Firm*—Cislo & Thomas LLP

(57) ABSTRACT

A skin treatment composition, comprising an effective combination of ingredients selected from cumin, cloves, peach kernel, olibanum, eagle wood, giant hyssop, almond, and pachira macracarpa is provided. The composition can be used as a skin cleanser, as a deodorant, and to treat a wide array of skin problems, including signs of aging, such as wrinkles, and skin sagging, dark spots, skin infections, skin irritation, cuts, scarring, acne, cold sores, chapped lips, and varicose veins.

10 Claims, No Drawings

SKIN TREATMENT COMPOSITION

CROSS-REFERENCES TO RELATED APPLICATIONS

This patent application claims priority from U.S. Provisional Patent Application Ser. No. 60/536,070 filed Jan. 12, 2004 for SKIN TREATMENT COMPOSITION, which application is incorporated herein by this reference thereto.

FIELD OF THE INVENTION

This invention relates to skin care composition providing beneficial effects.

BACKGROUND OF THE INVENTION

Expanding efforts are constantly made to find improved compositions which have beneficial skin treatment properties for treating a wide variety of possible skin disorders. Extracts of herbal and other natural plant ingredients such as clove oil, cumin oil and olibanum have been used in various skin care preparations. The beneficial effects of plant extracts are well recognized and new combinations providing improved skin treatment preparations are constantly being discovered.

SUMMARY OF THE INVENTION

The present invention provides a skin treatment composition, and is generally produced from cumin, cloves, olibanum, eagle wood, and giant hyssop, as base ingredients. Almond, peach kernel, pachira macracarpa, and a variety of other ingredients having beneficial properties may also be included in the composition.

The composition is preferably formulated in water, as a mud pack, or bath preparation. Other suitable delivery systems may be included. The composition can be used as a skin cleanser, as a deodorant, and to treat a wide array of skin problems, including signs of aging, such as wrinkles, and skin sagging, dark spots, skin infections, skin irritation, cuts, scarring, acne, cold sores, chapped lips, and varicose veins. The composition can further be used for hair treatment, to thicken hair roots, and to prevent hair loss. The composition can also be used for vaginal treatment, including for yeast and other infections, vaginal discharge, and to promote recovery after a vaginal birth and episiotomy. Such treatment is especially effective when the composition is used as a bath preparation. The composition further has a soothing and relaxing effect especially when used in a bath.

OBJECTS OF THE INVENTION

It is an object of the present invention to provide a skin treatment composition having a variety of beneficial effects, including providing treatment for aging, skin infections, hair loss, scarring dark spots, acne, cold sores, and varicose veins.

It is yet another object of the present invention to provide a skin treatment composition which can be used for the treatment of vaginal infections and to promote recovery after a vaginal birth.

It is yet another object of the present invention to provide a skin treatment composition which can be used as a skin cleanser and as a deodorant.

These and other objects and advantages of the present invention will be apparent from a review of the following specification and accompanying drawings.

DESCRIPTION OF THE PREFERRED EMBODIMENT(S)

The detailed description set forth below is intended as a description of presently-preferred embodiments of the invention and is not intended to represent the only forms in which the present invention may be constructed and/or utilized. The description sets forth the functions and the sequence of steps for practicing the invention in connection with the illustrated embodiments. However, it is to be understood that the same or equivalent functions and sequences may be accomplished by different embodiments that are also intended to be encompassed within the spirit and scope of the invention.

The composition of the present invention includes, as base ingredients, cumin, cloves, olibanum, eagle wood, and giant hyssop. Peach kernel, almond, pachira macracarpa schl nut, and a variety of other beneficial components may be added to the base ingredients. The ingredients are preferably formulated in water, as mudpack, or as a bath preparation, and may be further be combined with any suitable delivery system, and/or included in cosmetic and pharmaceutical preparations, such as hair care products, cosmetic products, creams, gels, lotions, emulsions, stick preparations, ointments, and the like. The ingredients may further be combined to form a paste, oil mixture, or the like, depending on the starting forms of the ingredients.

The composition is useful in treating a variety of skin related conditions including signs of aging, such as wrinkles, baggy eyes, and skin sagging, dark spots, skin infections, skin irritation, cuts, scarring, acne, cold sores, chapped lips, and varicose veins. The composition can also be used as a skin cleanser, as a deodorant, and for hair treatment, to thicken hair roots, and to prevent hair loss. The composition can further be used for vaginal treatment, including for yeast and other infections, vaginal discharge, and to promote recovery after a vaginal birth and episiotomy. Such treatment is especially effective when the composition is used in a bath preparation. The composition further has a soothing and relaxing effect especially when used in a bath.

Cumin is generally known for its beneficial uses as a skin treating agent, which include cleansing, shrinking or tightening, and for its oil removing properties. Clove is a known anti-inflammatory agent and has been particularly used to heal inflamed gums. The other base ingredients which include olibanum, also known as frankincense, eagle wood, and hyssop, which may be giant hyssop, and other preferred components including peach kernel, almond, which may be bitter almond, and pachira macracarpa, also known as moneytree, also have individual beneficial effects. However, a formulation containing the combined ingredients provides superior skin healing and beneficial properties, than any ingredient by itself. These ingredients may be in any convenient starting form, including oil, powder, fresh, dried, chopped, etc.

According to a preferred embodiment, the base ingredients which comprise cumin, cloves, olibanum, eagle wood, and giant hyssop are each present in a concentration of approximately 10–20 parts based on total composition weight (i.e., each in a relative ratio of 10:20 therein). Peach kernel, which is the part taken directly from the peach nut or pit, may be present at a lower concentration with respect to the base ingredients. A suitable concentration of peach kernel is approximately 0.1–10 parts, based on total composition weight, depending on the concentrations of the base ingredients. Almond may be present at a concentration which is in the order of approximately 5 to 10 times the concentrations of each of the base ingredients. A suitable concentration for the almond is 50–500 parts, based on total composition weight, depending on the concentrations of the base ingredients. Pachira macracarpa may be present at a concentration which is in the order of approximately 4 times the concentrations of each of the based ingredients. A suitable concentration for the pachira macracarpa is approximately 40 parts per total composition weight.

The composition may be prepared by mixing the base ingredients and other optional ingredients to preferably form a paste, oil, or other type of mixture depending on the form of the starting ingredients.

Additionally, the composition may be prepared by mixing the ingredients in water and heating and/or boiling the water mixture. The ratio of ingredients to water and amount of heating and/or boiling time may vary depending on the desired final concentration and other ingredients used. This results in distinct liquid and solid components, both of which can be applied to the skin. The liquid phase composition, which is more concentrated than the solid, can be added to a bath or applied to the skin, either directly, or using an application medium such as a sponge, cloth, cotton, or the like. The composition may either be left on the skin or rinsed off after a certain time period. Additionally, the liquid may be added to a delivery medium such as a cream, gel, lotion, paste, petroleum jelly, or the like. The solid form is preferably used as a mud pack, which can be applied to the skin, and left for a certain time period, preferably 15 to 20 minutes, then rinsed off.

Other ingredients having beneficial effects may be added to the composition for enhanced effects. For example, avocado may be added to a composition for treating acne. Wheat germ and egg yolk may be added to provide enhanced moisturizing and skin smoothing effects. Solanum nigrum linn may also be added for providing skin tone lightening effects. Egg white, and optionally milk and soy bean may be added for softening caulis spots. Crassocephalum crepidioides may be added to a composition used for hair treatment to prevent fading of hair color. Green beans may be added to neutralize the mixture. Cucumbers may also be added for beneficial effects. A variety of other components having known beneficial effects may be added to the base composition. The mixture of such components with the base composition enhances the beneficial effects of such components.

The following examples illustrate various composition and preparation methods in accordance with the present invention. For all listed examples, the starting is ingredients are preferably in crushed or powdered form, and boiling temperature may preferably be between 100 and 120 degrees.

EXAMPLE 1

Approximately 100 grams of almond in 4 cups of water (or in a ratio of about 10 grams almond for about every 95 ml of water) is boiled for approximately five minutes. A mixture of the base ingredients comprising about 15 grams (or in a ratio of about 1.5 grams base ingredients for about every 95 ml of water) of each of cumin, cloves, olibanum, eagle wood, and giant hyssop is then added. The resulting composition is stirred well and heated for another 5 to 10 minutes. Approximately 40 grams (or in a ratio of about 4 grams pachira macracarpa schl nut for every 95 ml of water) of pachira macracarpa schl nut is then added and the composition is stirred. The resulting composition is then heated for approximately another 2 minutes.

EXAMPLE 2

Approximately 50 grams of almond (or in a ratio of about 1 g almond for every 9.5 ml water) and approximately 50 grams of soybeans (or in a ratio of about 1 g soybeans for every 9.5 ml water) are heated in 2 cups of water for 5 minutes. Approximately 1 tablespoon of the base ingredients (or in a ratio of about 0.3 g base ingredients for every 9.5 ml water) comprising cumin, cloves, olibanum, eagle wood, and giant hyssop, in equal parts (by weight) is added to the composition. The resulting composition is then cooled. Next 2 raw egg whites are added, and the composition is mixed thoroughly. This forms a bath wash that removes old skin.

EXAMPLE 3

A composition including approximately 50 grams of almond (or about 1 g almond for every 4.7 ml water) in 1 cup of water is heated for 5 minutes. Next, approximately 1 tablespoon of the base ingredients (or in a ratio of about 0.3 g for every 4.7 ml water) comprising cumin, cloves, olibanum, eagle wood, and giant hyssop, in equal parts (by weight), is mixed into the composition. The resulting composition is allowed to cool to room temperature, and 3 raw egg yokes are added. The composition is the mixed thoroughly. This forms a paste that moisturizes and smoothes skin.

EXAMPLE 4

Approximately 1 teaspoon of the base ingredients, comprising cumin, cloves, olibanum, eagle wood, and giant hyssop, in equal parts (by weight), is mixed with 50 grams of mashed or pureed avocado to form a facial cream.

EXAMPLE 5

Approximately 1 cup of Solanum Nigrum Linn juice extract is mixed with 1 tablespoon of the base ingredients, comprising cumin, cloves, olibanum, eagle wood, and giant hyssop, in equal parts (by weight) (or in a ratio of about 0.6 g base ingredients per 9.5 ml Solanum Nigrum Linn juice extract). This forms a composition which can be added to a bath to induce skin tone lightening.

While the present invention has been described with regards to particular embodiments, it is recognized that additional variations of the present invention may be devised without departing from the inventive concept.

What is claimed is:

1. A skin-care and hair care composition comprising cumin, cloves, olibanum, eagle wood, and giant hyssop, each in a relative ratio amount of 10:20 therein.

2. The composition of claim 1, further comprising: at least one ingredient selected from the group consisting of avocado, solanum nigrum linn, wheat germ.

3. The composition of claim 1, further comprising pachira macracapra.

4. The composition of claim 1 wherein the cumin, cloves, olibanum, eagle wood and giant hyssop are present in equal weight proportions.

5. The composition of claim 4, further comprising almond and peach kernel, wherein the concentration of almond is between five and ten times the concentration of each of cumin, cloves, olibanum, eagle wood and giant hyssop and wherein the relative ratio amount of peach kernel is 0.1:10 therein.

6. The composition of claim 1, wherein the cumin, cloves, olibanum, eagle wood, and giant hyssop are present in equal amounts.

7. The composition of claim 6, further comprising solanum nigrum linn.

8. The composition of claim 7, further comprising pachira macracarpa, wherein the concentration of pachiira macracarpa is approximately four times the concentration of each of cumin, cloves, olibanum, eagle wood, and giant hyssop based on total composition weight.

9. The composition of claim 8 further comprising pachira macracarpa.

10. The composition of claim 6, further comprising almond and peach kernel, wherein the concentration of almond is between five and ten times the concentration of each of cumin, cloves, olibanum, eagle wood, and giant hyssop, and wherein the relative ratio amount of peach kernel is 0.1:10 therein.

* * * * *